United States Patent [19]
Pike

[11] Patent Number: 5,954,698
[45] Date of Patent: Sep. 21, 1999

[54] CATHETER APPARATUS HAVING VALVED CATHETER HUB AND NEEDLE PROTECTOR

[75] Inventor: Kevin H. Pike, Ypsilanti, Mich.

[73] Assignee: Vadus, Inc., Ann Arbor, Mich.

[21] Appl. No.: 08/778,234

[22] Filed: Jan. 8, 1997

[51] Int. Cl.[6] .................................................. A61M 5/178
[52] U.S. Cl. ........................ 604/169; 604/164; 604/264
[58] Field of Search ................................... 604/164, 167, 604/169, 192, 198, 263, 269, 264

[56] References Cited

U.S. PATENT DOCUMENTS

| | | | |
|---|---|---|---|
| 3,313,299 | 4/1967 | Spademan | 604/167 |
| 4,096,860 | 6/1978 | McLaughlin | 604/167 X |
| 4,211,741 | 7/1980 | Ostoich | 264/173 |
| 4,254,773 | 3/1981 | Waldbillig | 128/348 |
| 4,391,029 | 7/1983 | Czuba et al. | 29/450 |
| 4,424,833 | 1/1984 | Spector et al. | 137/849 |
| 4,512,766 | 4/1985 | Vailancourt | 604/169 |
| 4,540,411 | 9/1985 | Bodicky | 604/169 |
| 4,585,440 | 4/1986 | Tchervenkov et al. | 604/167 X |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,683,916 | 8/1987 | Raines | 137/854 |
| 4,713,057 | 12/1987 | Huttner et al. | 604/164 |
| 4,728,322 | 3/1988 | Walker et al. | 604/165 |
| 4,755,173 | 7/1988 | Konopka et al. | 604/167 |
| 4,781,703 | 11/1988 | Walker et al. | 604/264 |
| 4,801,295 | 1/1989 | Spencer | 604/198 |
| 4,832,696 | 5/1989 | Luther et al. | 604/164 |
| 4,846,805 | 7/1989 | Sitar | 604/165 |
| 4,850,961 | 7/1989 | Wanderer et al. | 604/53 |
| 4,883,699 | 11/1989 | Aniuk et al. | 428/36.9 |
| 4,917,669 | 4/1990 | Bonaldo | 604/164 |
| 4,944,728 | 7/1990 | Carrell et al. | 604/164 |
| 4,952,207 | 8/1990 | Lemieux | 604/164 |
| 5,000,740 | 3/1991 | Ducharme et al. | 604/162 |
| 5,013,304 | 5/1991 | Russell et al. | 604/167 |
| 5,019,049 | 5/1991 | Haining | 604/165 |
| 5,051,109 | 9/1991 | Simon | 604/263 |
| 5,078,689 | 1/1992 | Keller | 604/167 |
| 5,088,985 | 2/1992 | Deras | 604/192 |
| 5,088,986 | 2/1992 | Nusbaum | 604/195 |
| 5,088,987 | 2/1992 | Noonan, Jr. | 604/195 |
| 5,088,988 | 2/1992 | Talonn et al. | 604/198 |
| 5,092,845 | 3/1992 | Chang | 604/164 |
| 5,092,853 | 3/1992 | Couvertier, II | 604/195 |
| 5,102,394 | 4/1992 | Lasaitis et al. | 604/164 |
| 5,108,374 | 4/1992 | Lemieux | 604/164 |
| 5,127,905 | 7/1992 | Lemieux | 604/164 |
| 5,135,504 | 8/1992 | McLess | 604/164 |
| 5,171,230 | 12/1992 | Eland et al. | 604/250 |
| 5,171,231 | 12/1992 | Heilger | 604/263 |
| 5,176,650 | 1/1993 | Haining | 604/164 |
| 5,183,469 | 2/1993 | Capaccio | 604/192 |
| 5,188,597 | 2/1993 | Sweeney et al. | 604/110 |
| 5,188,607 | 2/1993 | Wu | 604/167 |
| 5,201,713 | 4/1993 | Rosetti | 604/165 |
| 5,215,525 | 6/1993 | Sturman | 604/164 |
| 5,215,527 | 6/1993 | Beck et al. | 604/164 |
| 5,215,528 | 6/1993 | Purdy et al. | 604/164 |
| 5,219,333 | 6/1993 | Sagstetter et al. | 604/110 |
| 5,226,899 | 7/1993 | Lee et al. | 604/282 |
| 5,234,416 | 8/1993 | Macaulay et al. | 604/282 |
| 5,240,537 | 8/1993 | Bodicky | 156/244.13 |
| 5,242,393 | 9/1993 | Brimhall et al. | 604/86 |
| 5,250,034 | 10/1993 | Appling et al. | 604/164 |
| 5,250,066 | 10/1993 | Lambert | 606/181 |
| 5,254,107 | 10/1993 | Soltesz | 604/282 |
| 5,261,885 | 11/1993 | Lui | 604/247 |
| 5,267,971 | 12/1993 | Brimhall | 604/177 |

(List continued on next page.)

*Primary Examiner*—John D. Yasko
*Attorney, Agent, or Firm*—Gardner, Carton & Douglas

[57] ABSTRACT

Catheter apparatus having a needle protector attached to a catheter hub. The needle protector includes a needle. The catheter hub defines a valve chamber. A valve is positioned in the chamber for controlling fluid flow through the chamber. The catheter apparatus is used to insert a catheter in a blood vessel and to regulate fluid flow between the catheter hub and the blood vessel.

24 Claims, 10 Drawing Sheets

U.S. PATENT DOCUMENTS

| | | | |
|---|---|---|---|
| 5,267,979 | 12/1993 | Appling et al. | 604/247 |
| 5,273,543 | 12/1993 | Bell et al. | 604/110 |
| 5,279,590 | 1/1994 | Sinko et al. | 604/263 |
| 5,279,591 | 1/1994 | Simon | 604/263 |
| 5,300,048 | 4/1994 | Drewes, Jr. et al. | 604/280 |
| 5,304,136 | 4/1994 | Erskine et al. | 604/110 |
| 5,304,140 | 4/1994 | Kugo et al. | 604/281 |
| 5,304,144 | 4/1994 | Brimhall | 604/177 |
| 5,304,149 | 4/1994 | Morigi | 604/192 |
| 5,304,155 | 4/1994 | Lui | 604/247 |
| 5,306,253 | 4/1994 | Brimhall | 604/165 |
| 5,308,330 | 5/1994 | Grimard | 604/110 |
| 5,312,361 | 5/1994 | Zadini et al. | 604/165 |
| 5,312,371 | 5/1994 | Dombrowski et al. | 604/198 |
| 5,316,706 | 5/1994 | Muni et al. | 264/25 |
| 5,318,547 | 6/1994 | Altschuler | 604/198 |
| 5,328,473 | 7/1994 | Fayngold et al. | 604/110 |
| 5,334,144 | 8/1994 | Alchas et al. | 604/68 |
| 5,338,310 | 8/1994 | Lewandowski | 604/192 |
| 5,342,309 | 8/1994 | Hausser | 604/110 |
| 5,344,404 | 9/1994 | Benson | 604/110 |
| 5,344,408 | 9/1994 | Partika | 604/192 |
| 5,356,390 | 10/1994 | Erskine | 604/164 |
| 5,370,624 | 12/1994 | Edwards et al. | 604/169 |
| 5,376,073 | 12/1994 | Graves et al. | 604/86 |
| 5,380,298 | 1/1995 | Zabetakis et al. | 604/265 |
| 5,380,307 | 1/1995 | Chee et al. | 604/264 |
| 5,385,554 | 1/1995 | Brimhall | 604/168 |
| 5,385,555 | 1/1995 | Hausser | 604/280 |
| 5,395,341 | 3/1995 | Slater | 604/164 |
| 5,397,512 | 3/1995 | Sloane, Jr. et al. | 264/25 |
| 5,405,323 | 4/1995 | Rogers et al. | 604/53 |
| 5,405,326 | 4/1995 | Haber et al. | 604/110 |
| 5,407,431 | 4/1995 | Botich et al. | 604/110 |
| 5,409,461 | 4/1995 | Steinman | 604/110 |
| 5,409,463 | 4/1995 | Thomas | 604/167 |
| 5,409,644 | 4/1995 | Martin et al. | 264/25 |
| 5,411,486 | 5/1995 | Zadini et al. | 604/198 |
| 5,415,184 | 5/1995 | Peck | 128/880 |
| 5,417,668 | 5/1995 | Setzer et al. | 604/263 |
| 5,419,766 | 5/1995 | Chang et al. | 604/110 |
| 5,419,777 | 5/1995 | Hofling | 604/264 |
| 5,423,758 | 6/1995 | Shaw | 604/110 |
| 5,423,766 | 6/1995 | Di Cesare | 604/192 |
| 5,423,773 | 6/1995 | Jimenez | 604/282 |
| 5,425,712 | 6/1995 | Goodin | 604/96 |
| 5,425,735 | 6/1995 | Rosen et al. | 606/128 |
| 5,425,903 | 6/1995 | Sloane, Jr. et al. | 264/22 |
| 5,429,613 | 7/1995 | D'Amico | 604/198 |
| 5,429,617 | 7/1995 | Hammersmark et al. | 604/264 |
| 5,435,314 | 7/1995 | Dias | 128/662.06 |
| 5,437,648 | 8/1995 | Graves et al. | 604/263 |
| 5,441,489 | 8/1995 | Utsumi et al. | 604/280 |
| 5,443,457 | 8/1995 | Ginn et al. | 604/280 |
| 5,445,619 | 8/1995 | Burns | 604/192 |
| 5,445,624 | 8/1995 | Jimenez | 604/280 |
| 5,446,230 | 8/1995 | Travers et al. | 585/748 |
| 5,447,501 | 9/1995 | Karlsson et al. | 604/198 |
| 5,447,503 | 9/1995 | Miller | 604/280 |
| 5,447,724 | 9/1995 | Helmus et al. | 424/426 |
| 5,449,349 | 9/1995 | Sallee et al. | 604/180 |
| 5,453,095 | 9/1995 | Davila et al. | 604/167 |
| 5,453,099 | 9/1995 | Lee et al. | 604/282 |
| 5,456,668 | 10/1995 | Ogle, II | 604/110 |
| 5,456,674 | 10/1995 | Bos et al. | 604/280 |
| 5,458,658 | 10/1995 | Sircom | 604/192 |
| 5,462,533 | 10/1995 | Daugherty | 604/164 |
| 5,464,398 | 11/1995 | Haindl | 604/280 |
| 5,464,399 | 11/1995 | Boettger | 604/283 |
| 5,472,430 | 12/1995 | Vaillancourt et al. | 604/198 |
| 5,474,539 | 12/1995 | Costa et al. | 604/164 |
| 5,478,313 | 12/1995 | White | 604/110 |
| 5,478,328 | 12/1995 | Silverman et al. | 604/272 |
| 5,487,732 | 1/1996 | Jeffrey | 604/110 |
| 5,520,654 | 5/1996 | Wahlberg | 604/164 |
| 5,531,701 | 7/1996 | Luther | 604/165 |
| 5,562,631 | 10/1996 | Bogert | 604/164 |

CATHETER APPARATUS HAVING VALVED CATHETER HUB AND NEEDLE PROTECTOR

BACKGROUND OF THE INVENTION

The present invention relates to a catheter apparatus. More specifically, the invention is directed to a catheter apparatus having a catheter hub and a needle protector. The catheter apparatus is used to, among other things, insert a catheter in a blood vessel of a patient.

Catheter insertion apparatus is known in the art. This prior art apparatus has many problems. First, the catheter hub does not include a valve for controlling or regulating fluid flow through the catheter hub. Second, the apparatus does not include a needle protector with dual handles that allows the needle to be accurately positioned during insertion of the catheter in the blood vessel and retraction of the needle into the needle protector. Third, the apparatus does not include a shape that provides ease in handling during use. Therefore, there is a need for a "bloodless" catheter apparatus that includes an internal valve in the catheter hub to regulate fluid flow, a needle protector that includes dual handles for accurate manipulation of the needle, and an apparatus that is shaped for easy handling during use. The present invention satisfies the above-identified needs.

SUMMARY OF THE INVENTION

The catheter apparatus of the present invention has a needle protector including a body having a first end and a second end. The body includes a plurality of side walls extending between the first and second ends in a first geometric configuration. The side walls define an interior space. The side walls define a first slot and a second slot. A needle hub having a front end, a back end, a first side and a second side is positioned in the internal space. The front end is adapted to receive a needle. The first and second sides each includes a handle. The handles extend through the slots to positions outside of the body. A needle is in communication with the front end of the needle hub.

The catheter apparatus further has a catheter hub including a housing having a connection end defining a first fluid passageway and a catheter end defining a second fluid passageway. The housing includes a plurality of hub walls arranged in a second geometric configuration. A valve is positioned in the valve chamber for regulating fluid flow through the chamber between the first and second fluid passageways. An actuator actuates the valve.

The primary object of the present invention is to provide a catheter apparatus that includes a valve for regulating fluid flow in the catheter hub.

An important object of the present invention is to provide a needle protector that includes dual handles for accurate manipulation of the needle.

Another important object of the present invention is to provide a catheter apparatus having a unique profile that aids in the insertion of a catheter in a blood vessel.

Other objects and advantages of the present invention will become apparent to those skilled in the art upon a review the following detailed description of the preferred embodiment and the accompanying drawings.

DETAILED DESCRIPTION OF THE PREFERRED EMBODIMENT

The preferred embodiment and best mode of the present invention will now be described in detail with reference being made to the drawings. The catheter apparatus of the present invention is indicated generally in the drawings by the reference number "1". The catheter apparatus includes a needle protector 10 and a catheter hub 110.

Figure 3:
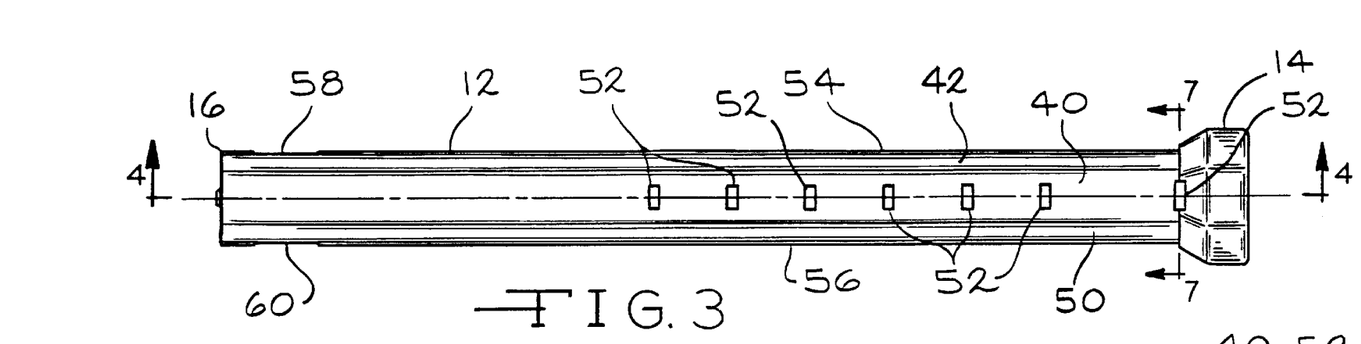
FIG. 3 is a top view of the body of the needle protector.
Figure 4:
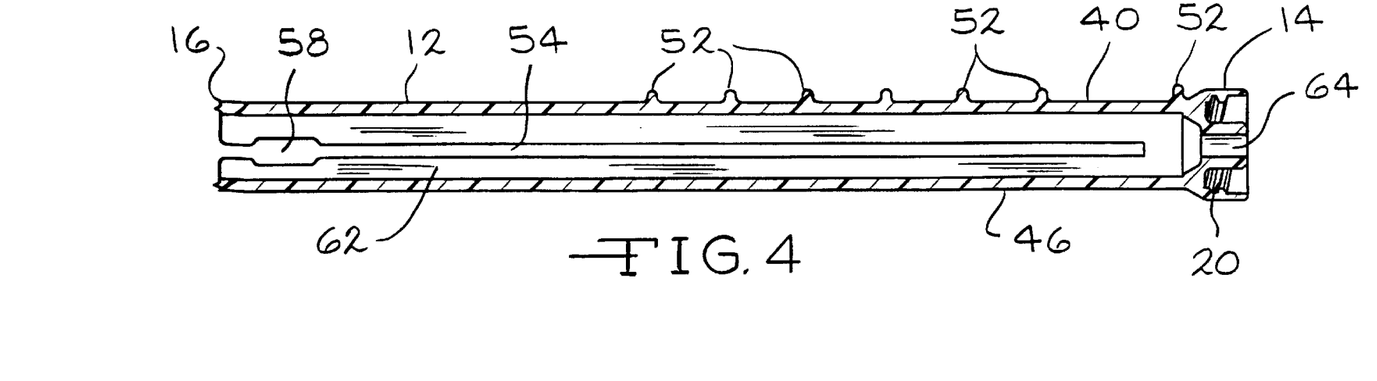
FIG. 4 is a cross-sectional view taken along line 4—4 of FIG. 3.
Figure 5:
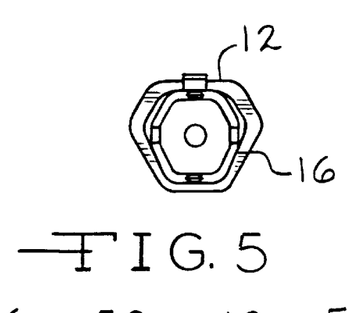
FIG. 5 is an elevational view of the second end of the body of the needle protector.
Figure 6:
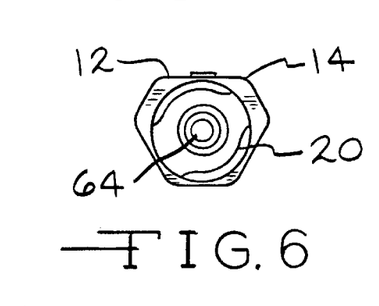
FIG. 6 is an elevational view of the first end of the body of the needle protector.

Referring to FIGS. 1–7 and 22–25, the needle protector 10 includes a body 12 having a first end 14 and a second end 16. As shown in FIGS. 1, 2, 4 and 6, the first end 14 is attached to receive a catheter hub 110. The first end 14 includes a plurality of threads 20, as shown in FIGS. 4 and 6, for receiving mating threads on the catheter hub 110, as described below, for attaching the needle protector 10 to the catheter hub. The first end 14 and the threads 20 are usually constructed to conform with American National Standard Institute No. ANSI/HIMA MD70.1-1983 relating to luer lock fittings, which is incorporated herein by reference.

Figure 8:
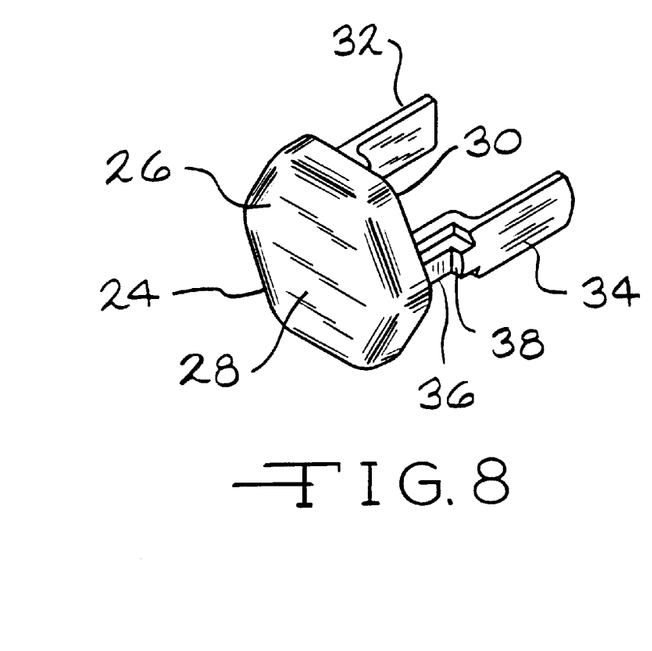
FIG. 8 is a perspective view of the end cap according to the present invention.
Figure 9:
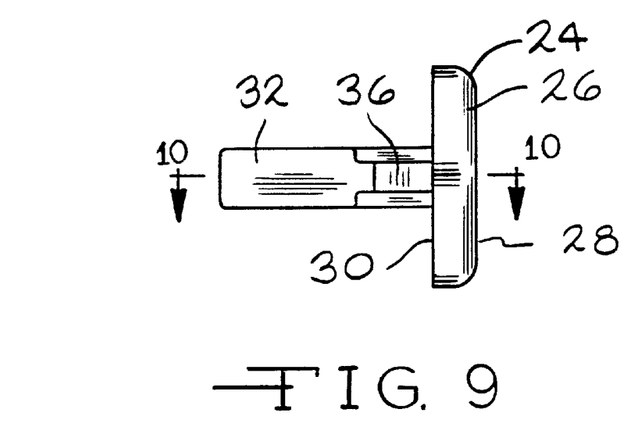
FIG. 9 is a side elevational view of the end cap shown in FIG. 8.
Figure 10:
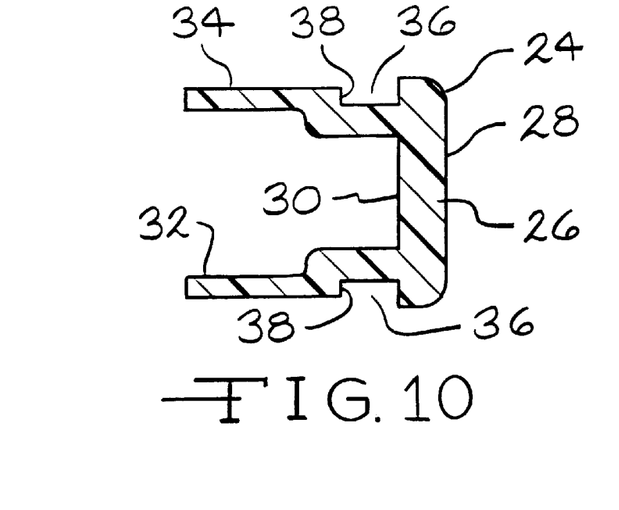
FIG. 10 is a cross-sectional view taken along line 10—10 of FIG. 9.
Figure 24:
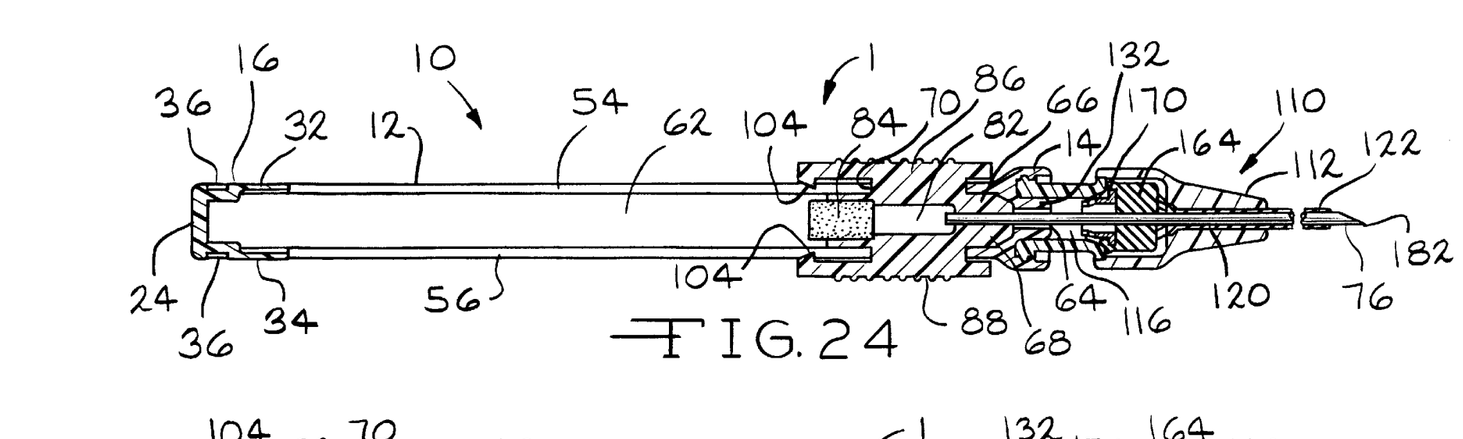
FIG. 24 is a cross-sectional top view of the catheter apparatus according to the present invention with the needle hub of the needle protector positioned at the first end of the needle protector.

As shown in FIGS. 1, 4, 5 and 8–10, the second end 16 of the body 12 is adapted to receive an end cap 24. As shown in FIGS. 8–10, the cap 24 includes a head 26 having an exterior surface 28 and an interior surface 30. A first leg 32 and a second leg 34 extend outwardly from the interior surface 30 of the head 26. As shown in FIG. 10, each of the first and second legs 32 and 34 includes a locking recess 36 having a locking surface 38. As shown in FIG. 24, the first and second legs 32 and 34 are inserted in the second end 16 of the body 12 to attach the cap 24 to the body.

Figures 1, 2:
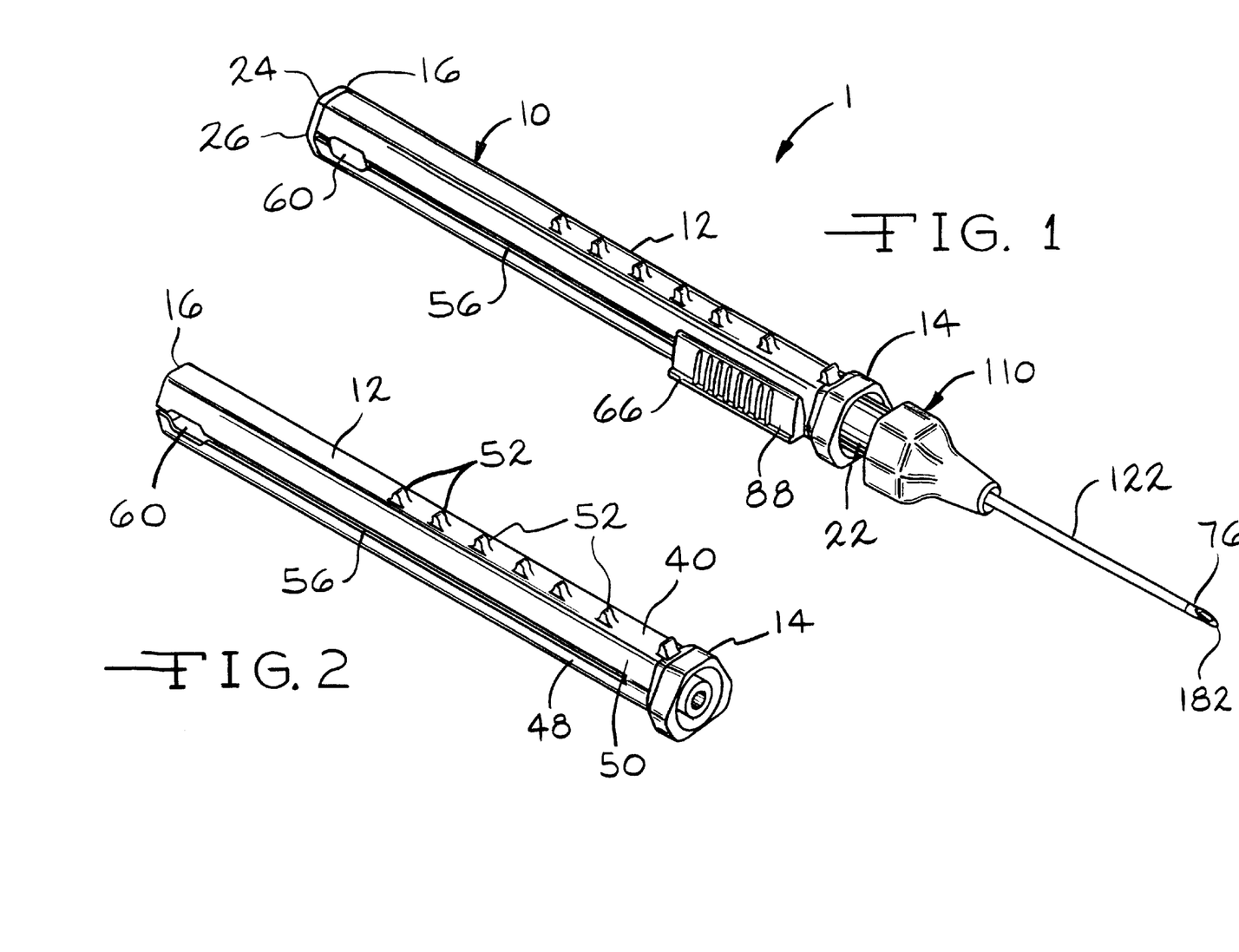
FIG. 1 is a perspective view of a catheter apparatus according to the present invention.
FIG. 2 is a perspective view of the body of the needle protector.
Figure 7:
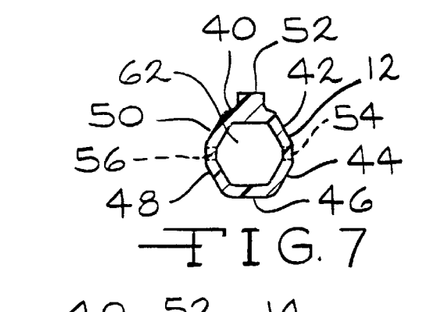
FIG. 7 is a cross-sectional view taken along line 7—7 of FIG. 3.

Referring to FIGS. 2, 3, 4 and 7, the body 12 includes a plurality of side walls extending between the first end 14 and the second end 16 in a first geometric configuration. In the preferred embodiment, as shown in FIG. 7, the body 12 includes a first side wall 40, a second side wall 42, a third side wall 44, a fourth side wall 46, a fifth side wall 48 and a sixth side wall 50. The side walls 40-50, are arranged to form a hexagonal configuration. It should be understood that the number of side walls of the body 12 can be varied to form other polygonal configurations, with a hexagonal configuration being preferred. As described below, the hexagonal configuration allows the needle protector 10 to be easily handled during use. For example, the fourth side wall 46 provides a flat, smooth surface for contact with, for example, the skin of a patient. The first side wall 40 provides a surface upon which, for example, the thumb of a person using the needle protector 10 can engage during handling. As shown in FIGS. 2, 3 and 4, a plurality of spaced upwardly extending projections 52 are positioned on the first side wall 40. The projections 52 may be engaged by a thumb to more accurately and easily handle the catheter apparatus 1.

Referring to FIGS. 2, 4 and 7, the side walls of the body 12 define at least two slots. In the preferred embodiment, second and third side walls 42 and 44 define a first slot 54, and the fifth and sixth side walls 48 and 50 define a second slot 56. The first and second slots 54 and 56 extend longitudinally between the first end 14 and the second end 16 of the body 12 in an opposed relationship to one another. As shown in FIGS. 2–4, the first and second slots 54 and 56 define first and second locking portions 58 and 60, respectively, adjacent the second end 16 of the body 12 in opposed relationship to one another. The first and second locking portions 58 and 60 are positioned adjacent the locking recesses 36 of the first and second legs 32 and 34 of the end cap 24.

Referring to FIGS. 4 and 7, the side walls 40–50 define an interior space 62 extending between the first and second ends 14 and 16 of the body 12. As shown in FIGS. 4 and 6, a needle opening 64 is defined by the body 12 at the first end 14. The needle opening 64 extends from the exterior of the body 12 to the interior space 62.

Figure 13:
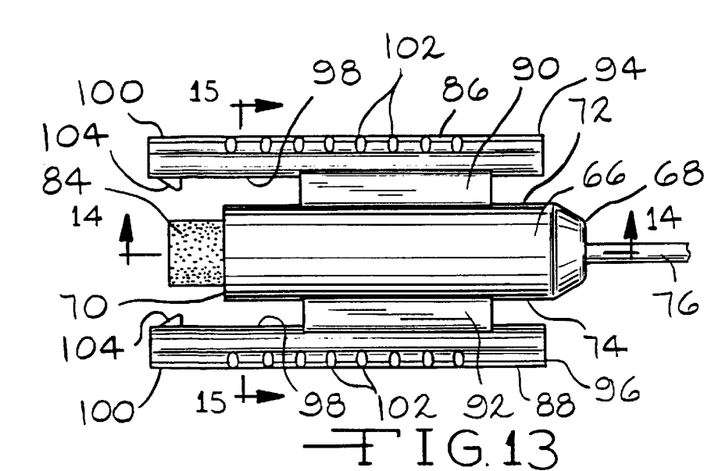
FIG. 13 is a top view of the needle hub according to the present invention.
Figure 14:
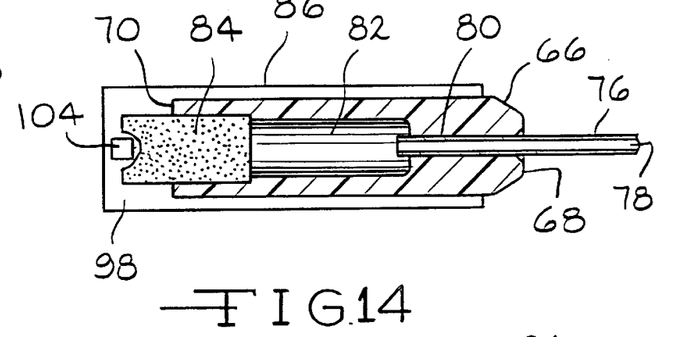
FIG. 14 is a cross-sectional view taken along line 14—14 of FIG. 13.
Figure 15:
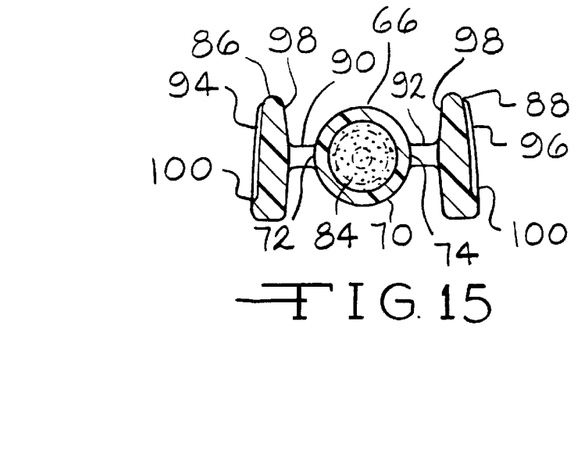
FIG. 15 is a cross-sectional view taken along line 15—15 of FIG. 13.
Figure 16:
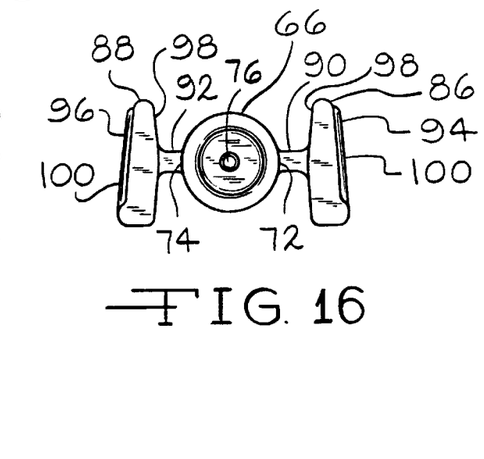
FIG. 16 is an elevational view of the back end of the needle hub.

Referring to FIGS. 11–17 and 22–25, the needle protector 10 includes a needle hub 66 having a front end 68, a back end 70, a first side 72 and second side 74. As shown in FIGS. 22–25, the needle hub 66 is movably positioned in the interior space 62 of the body 12. As shown in FIG. 14, the front end 68 of the needle hub 66 is adapted to receive a hollow needle 76 defining a needle fluid passageway 78. The front end 68 includes a front end opening 80 for receiving the needle 76. The needle hub 66 defines a hub fluid passageway 82 extending between the front and back ends 68 and 70. The needle 76 is positioned in the front end opening 80 so that the needle fluid passageway 78 is in communication with the hub fluid passageway 82. As shown in FIGS. 13 and 14, the back end 70 of the needle hub 66 includes absorbent material 84. The absorbent material 84 absorbs any fluid, such as blood, contained in the hub fluid passageway 82.

Referring to FIGS. 13, 15, 16 and 25, the first and second sides 72 and 74 of the needle hub 66 include first and second handles 86 and 88, respectively. The first and second handles 86 and 88 include first and second wings 90 and 92, respectively. The first and second wings 90 and 92 extend from the needle hub 66 through the first and second slots 54 and 56, respectively, to the exterior of the body 12.

Still referring to FIGS. 13, 15, 16 and 25, the first and second handles 86 and 88 include first and second handle members 94 and 96, respectively, attached to the first and second wings 90 and 92, respectively. Each of the first and second handle members 94 and 96 includes an interior surface 98 and an exterior surface 100. As shown in FIG. 13, each exterior surface 100 includes a plurality of spaced grips 102. The grips 102 allow the first and second handles 86 and 88 to be firmly gripped during actuation of the needle hub 66.

Figure 17:
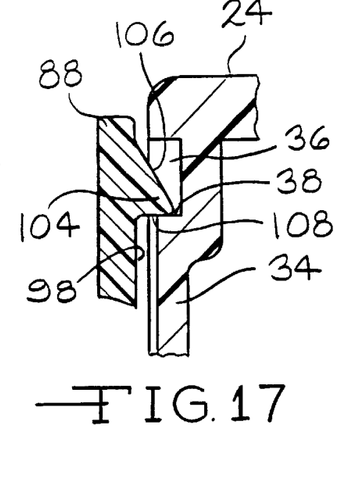
FIG. 17 is a cross-sectional view taken along line 17—17 of FIG. 11.
Figure 25:
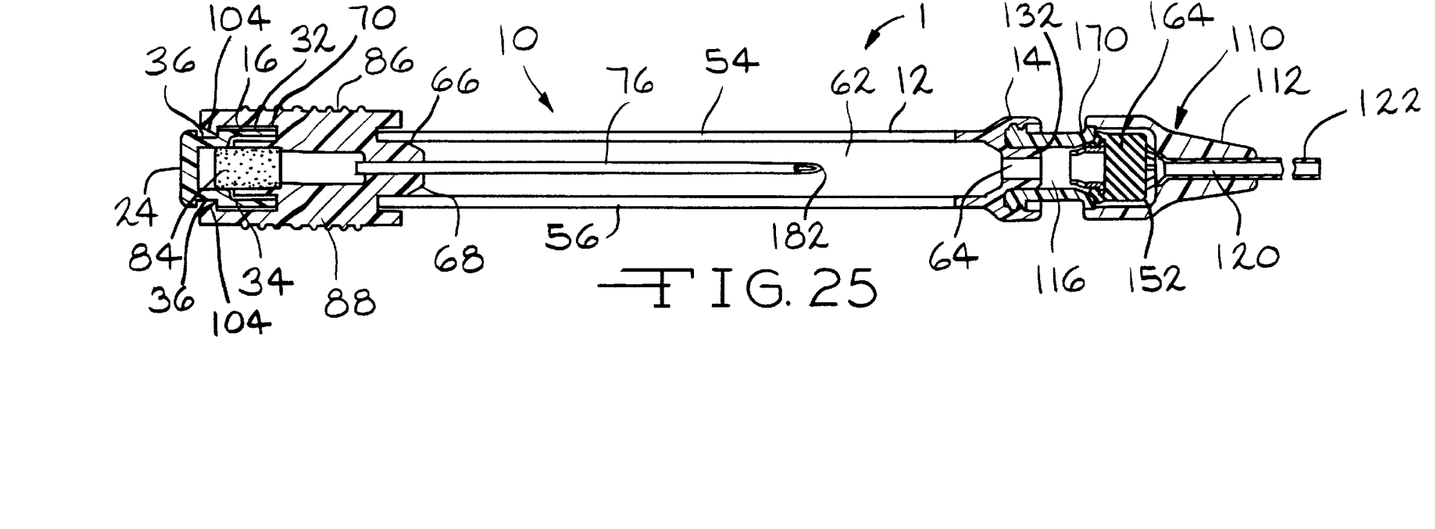
FIG. 25 is a view similar to the view of FIG. 24 with the needle hub positioned at the second end of the needle protector.

Referring to FIGS. 13, 17 and 25, the first and second handle members 94 and 96 each includes a locking projection 104 extending inwardly from the interior surface 98. As shown in FIG. 17, each locking projection 104 includes a ramp surface 106 and a locking surface 108. The locking projections 104 are received by the locking recesses 36 of the first and second legs 32 and 34. The locking surfaces 108 of the locking projections 104 engage the recess surfaces 38 of the locking recesses 36 to lock the needle hub 66 to the second end 1 6 of the body 12. This prevents the needle hub 66 from being moved toward the first end 14 thus preventing movement of the needle 74 from the interior space 62 of the body 12.

Figures 18, 19, 19A:
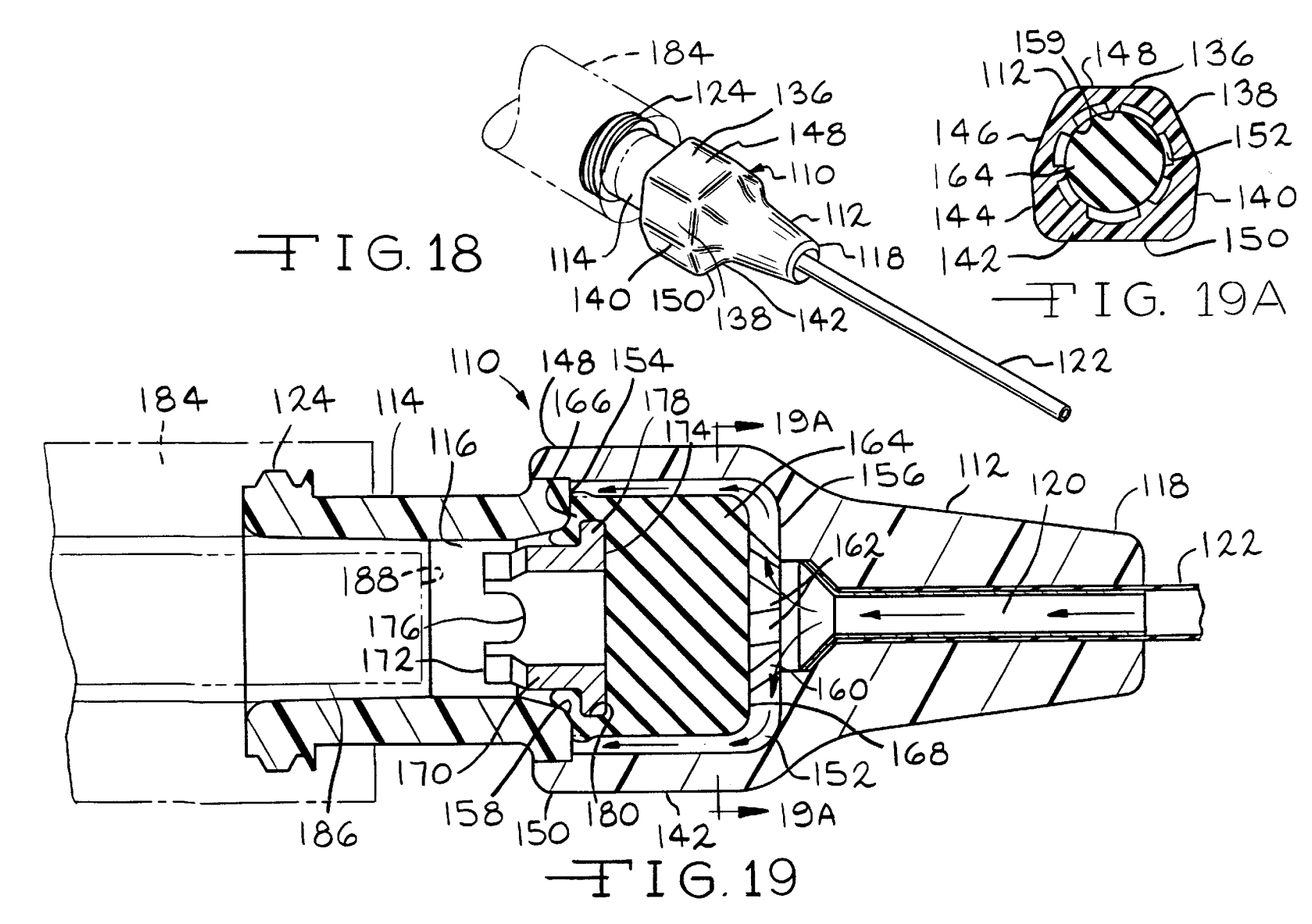
FIG. 18 is a perspective view of the catheter hub according to the present invention connected to a standard luer fitting.
FIG. 19 is a cross-sectional view taken through the center of the catheter hub with the valve in a closed position.
FIG. 19A is a cross-sectional view taken along line 19A—19A of FIG. 19.

Referring to FIGS. 18–25, the catheter hub 110 of the catheter apparatus 1 includes a housing 112 having a connection end 114 defining a first fluid passageway 116 and a catheter end 118 defining a second fluid passageway 120. As shown in FIG. 19, the catheter end 118 includes a catheter 122 consisting of a polymeric material positioned in the second fluid passageway 120. The connection end 114 includes a plurality of threads 124. The connection end 114 and the threads 124 are usually constructed to conform with American National Standard Institute No. ANSI/HIMA MD70.1-1983 relating to luer lock fittings.

Figure 21:
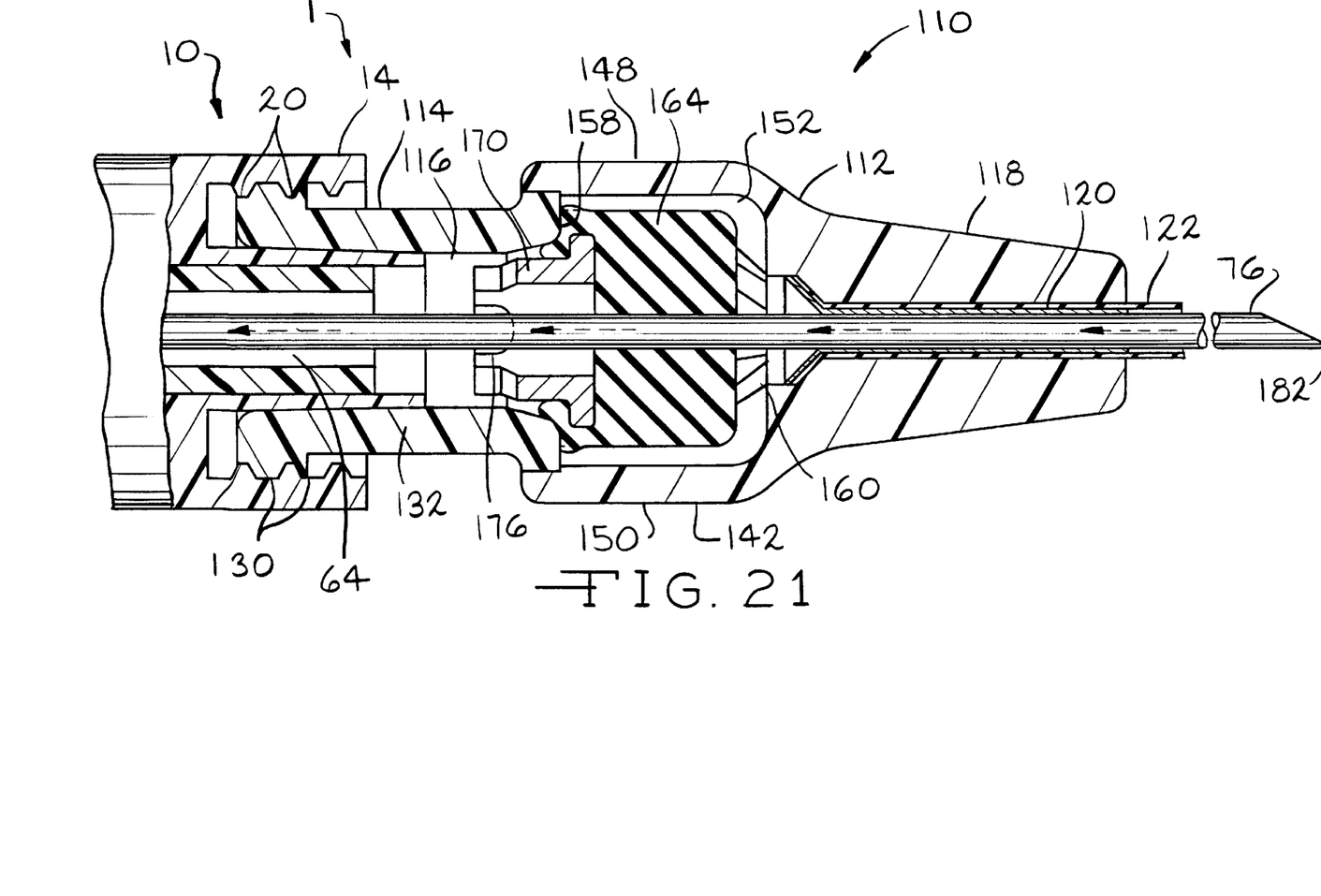
FIG. 21 is a cross-sectional view taken through the center of the catheter hub according to the present invention attached to the first end of the needle protector with the needle extending from the needle protector through the catheter hub.

Referring to FIGS. 1, 11 and 21–25, the catheter hub 110 is attached to the needle protector 10. The plurality of threads 20 of the first end 14 of the needle protector 10 mates with the plurality of threads 124 of the housing 112. As shown in FIG. 21, the needle protector 10 includes a needle protector projection 132 that extends into the first fluid passageway 116. The needle 76 of the needle protector 10 extends through the catheter hub 110.

Referring to FIGS. 19 and 19A, the housing 112 includes a plurality of hub walls arranged in a second geometric configuration. In the preferred embodiment, as shown in FIG. 19A, the housing 112 includes a first hub wall 136, a second hub wall 138, a third hub wall 140, a fourth hub wall 142, a fifth hub wall 144 and a sixth hub wall 146. As shown in FIGS. 19 and 19A, the housing 112 includes a top 148 and a bottom 150. The fourth hub wall 142 is positioned at the bottom 150 of the housing 112. When so positioned, the fourth hub wall 142 is planar. The planar surface provided by the fourth hub wall 142 provides a flat, smooth surface that can rest against the skin of a patient during use of the catheter hub 110. As described below, this allows the catheter hub 110 to be easily positioned at the site of the blood vessel into which the catheter 122 is to be inserted. As shown in FIG. 19A, the geometric configuration formed by the hub walls 136–146 is a hexagon. However, it should be understood that a variety of polygonal configurations may be used as long as there is a planar surface adjacent the bottom 148 of the housing 112.

Still referring to FIGS. 19 and 19A, the hub walls 136–146 define a valve chamber 152 having a shoulder end 154 and a passageway end 156. As shown in FIG. 19, the connection end 114 of the housing 112 defines an annular shoulder 158 adjacent the shoulder end 154 of the valve chamber 152. As shown in FIG. 19A, the housing 112 defines a plurality of inwardly extending valve ribs 159 in the valve chamber 152. A valve seat 160 is positioned in the valve chamber 152 adjacent the passageway end 156. The valve seat 160 defines a plurality of fluid openings 162 that allows for fluid flow between the second fluid passageway 120 defined by the catheter end 118 of the housing 112 and the valve chamber 152.

As shown in FIGS. 19 and 19A, the catheter hub 110 includes a valve 164 positioned in the valve chamber 152 adjacent the valve ribs 159. The valve 164 is comprised of a resilient material having a substantially cylindrical configuration. As shown in FIG. 19, the valve 164 has an actuator end 166 and a housing end 168. When the valve 164 is in its normally closed position, as shown in FIG. 19, the actuator end 166 is engaged with the annular shoulder 158 of the connection end 114. This engagement acts to seal the valve chamber 152 from the first fluid passageway 116 defined by the connection end 114 of the housing 112. The housing end 168 of the valve 164 engages the valve seat 160. The valve 164 can consist of a variety of resilient materials, with rubber, silicon and polyisoprene being preferred.

Referring to FIG. 19, the catheter hub 110 includes an actuator 170 that is positioned in the first fluid passageway 116. The actuator 170 includes a luer end 172 and a valve end 174. The actuator 170 is free to move within the first fluid passageway 116 and the valve chamber 152. The actuator 170 defines a needle passageway 176 that extends longitudinally between the luer and valve ends 172 and 174. As shown in FIG. 19, the valve end 174 of the actuator 170 includes an annular flange 178 that is received by a recess 180 defined by the valve 164 at the actuator end 166. This allows a portion of the valve 164 to be positioned between the annular shoulder 158 and the annular flange 178. The annular flange 178 provides structural support for the valve 164 at the actuator end 166 so that a superior seal is formed.

Figure 22:
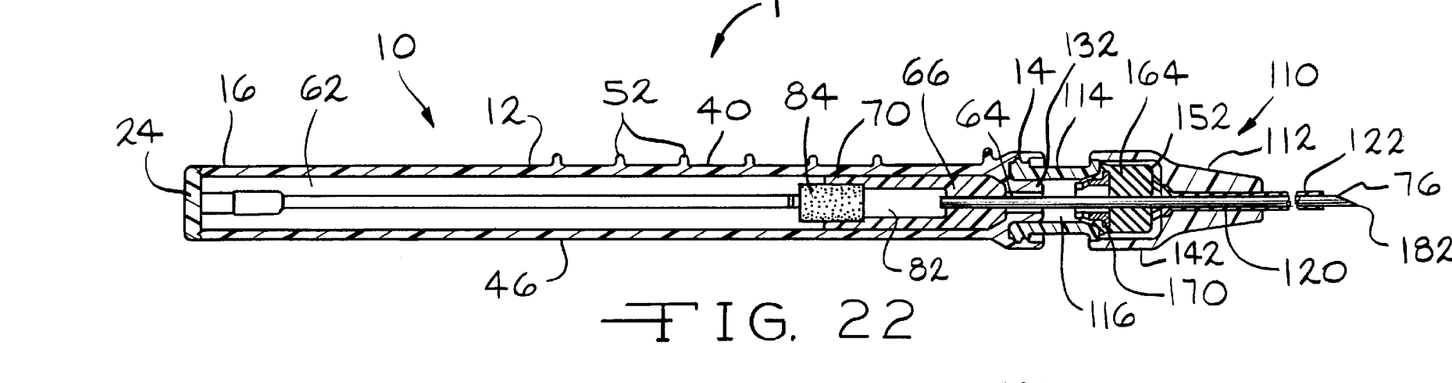
FIG. 22 is a cross-sectional side elevational view taken through the center of the catheter apparatus according to the present invention with the needle hub of the needle protector positioned at the first end of the needle protector.

The operation and intended use of the catheter apparatus 1 will now be described. As shown in FIGS. 21, 22 and 24, the catheter hub 110 is attached to the needle protector 10 by insertion of the projection 132 into the first fluid passageway 116 and the mating of the threads 20 and 130. The projection 132 is adapted so that it does not move the actuator 170 to actuate the valve 164 regardless of the travel of the projection into the first fluid passageway 11 6. As shown in FIGS. 21, 22 and 24, the needle 76 of the needle protector 10 extends through the needle opening 64 of projection 132, into the needle passageway 176 of the actuator 170, the valve 164, the valve seat 160, the catheter 122 to the exterior of the catheter hub 110. When so positioned, the pointed end 182 of the needle 76 can be inserted in the blood vessel of the patient (not shown).

During use of the catheter apparatus 1, the fourth wall 142 of the housing 112, which provides a planar surface, and the fourth side wall 46 of the needle protector 10 are positioned on the skin of the patient adjacent the injection site. This allows the catheter apparatus 1 to be easily moved along the skin during insertion of the needle 76 into the blood vessel.

When the catheter 122 is to be inserted in the blood vessel, the user of the catheter apparatus 1 grips the body 12 of the needle protector 10 and places his or her index finger on the first side wall 40. The finger engages the projections 52 so that the body 12 can be accurately positioned with respect to the blood vessel. When the pointed end 182 of the needle 76 is properly positioned, the user pushes the pointed end into the blood vessel. Blood from the blood vessel "flashes" or enters the needle fluid passageway 78 of the needle 76 and then proceeds to the hub fluid passageway 82. The absorbent material 84 absorbs the blood to prevent leakage from the needle hub 66. Insertion of the needle 76 into the blood vessel results in the insertion of the catheter 122 into the blood vessel.

Figures 11, 12:
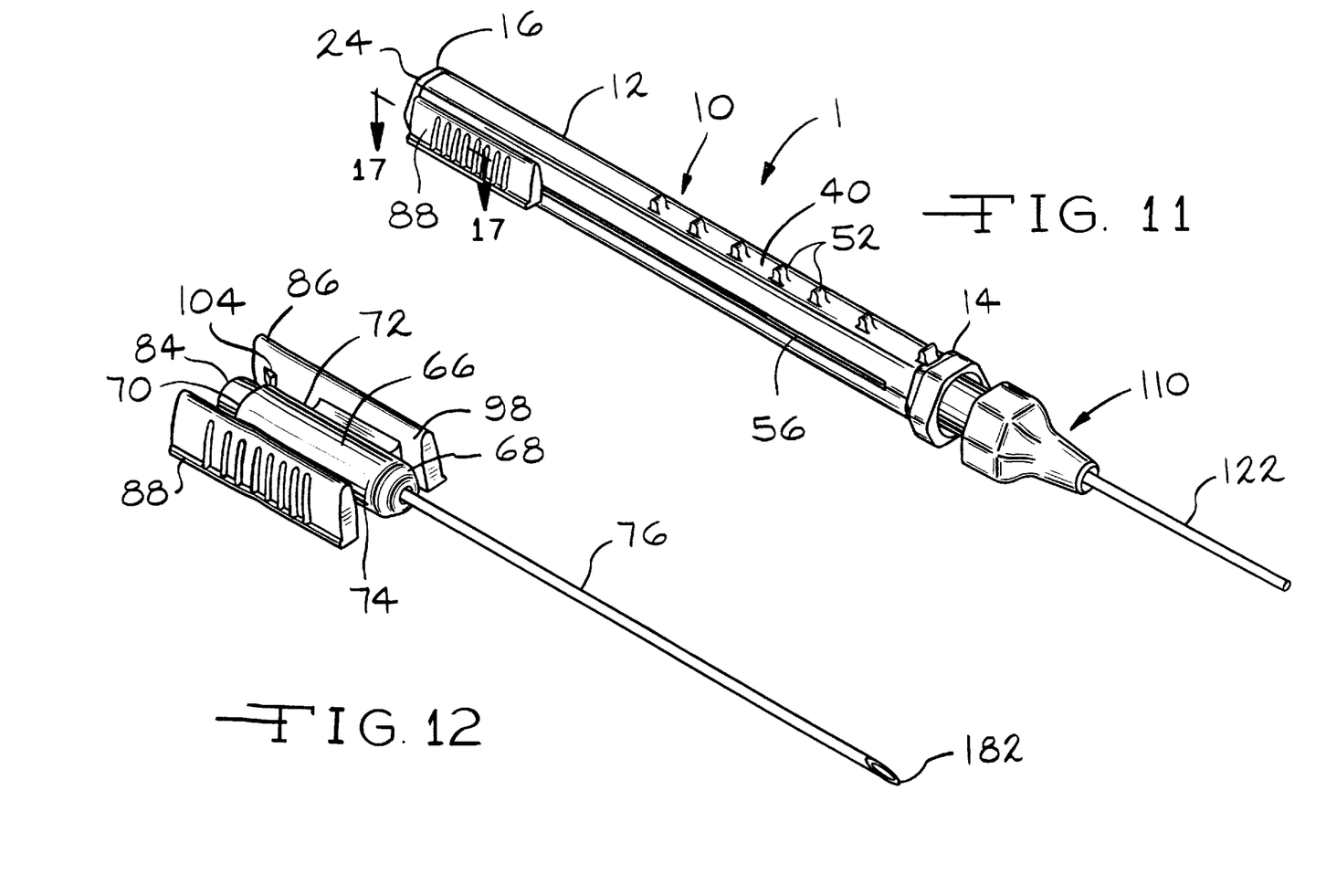
FIG. 11 is a view similar to the view of FIG. 1 in which the needle hub according to the present invention has been moved from the first end of the body to the second end of the body.
FIG. 12 is a perspective view of the needle hub and needle according to the present invention.
Figure 23:
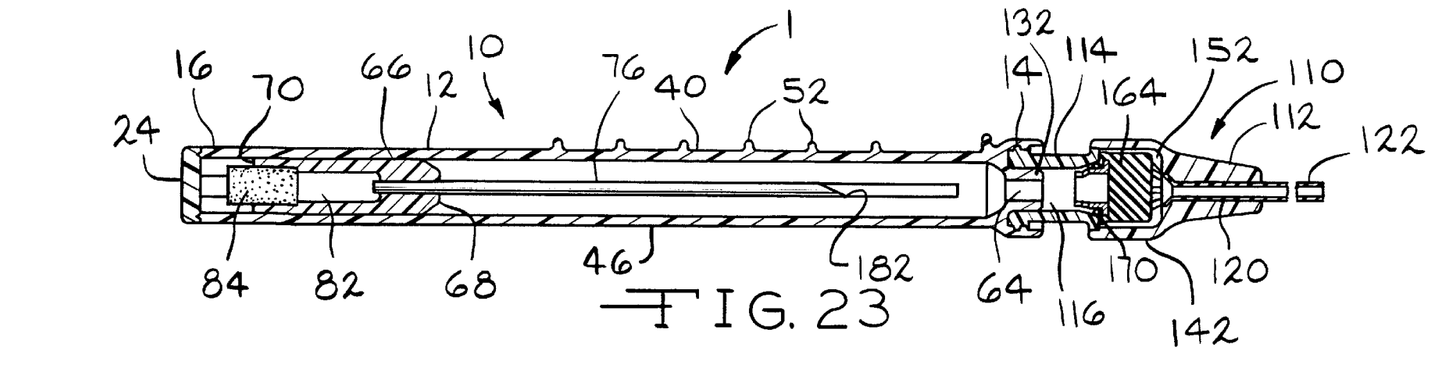
FIG. 23 is a view similar to the view of FIG. 22 with the needle hub positioned at the second end of the needle protector.

Referring to FIGS. 11 and 17, after the catheter 122 has been inserted, the user of the catheter apparatus 1 causes his or her thumb and forefinger to engage the first and second handles 86 and 88 of the needle hub 66. The grips 102 prevent slippage by the user. The user pulls back on the first and second handles 86 and 88 thereby causing the needle hub 66 to move from the first end 14 to the second end 16 of the body 12. The first and second wings 90 and 92 travel along the first and second slots 54 and 56, respectively, to guide the needle hub 66 along its predetermined path. The first and second wings 90 and 92 maintain the needle hub 66 in proper axial alignment with respect to the body 12. Movement of the needle hub 66 causes corresponding movement of the needle 76. Retraction of the needle 76 into the needle protector 10 results in the needle 76 being retracted from the catheter 122, the valve seat 160, the valve 164, the actuator 170 and the first fluid passageway 116. As the needle hub 66 moves toward the second end 16 of the needle protector 10, the needle 76 passes through the needle opening 64 into the interior space 62 of the body 12. As shown in FIGS. 23 and 25, when the needle hub 66 is positioned adjacent the second end 16 of the body 12, the needle 76 is fully contained in the interior space 62. As shown in FIGS. 17 and 25, the locking projections 104 are received by the locking recesses of the cap 24 to prevent forward movement of the needle hub 66. The engagement of the locking surfaces 108 with the recess surfaces 38 provides a positive lock so that the needle 76 cannot exit through the needle opening 64. After the needle 76 has been locked in place, the user of the catheter apparatus 1 disengages the needle protector 10 from the catheter hub 110.

As shown in FIG. 19, blood moving in the direction indicated by the arrows through the second fluid passageway 120, the valve seat 1 60 and the valve chamber 152 is prevented from entering the first fluid passageway 116 due to the seal created between the valve 164 and the annular shoulder 158. This prevents leakage of blood to the exterior of the catheter hub 110.

Figure 20:
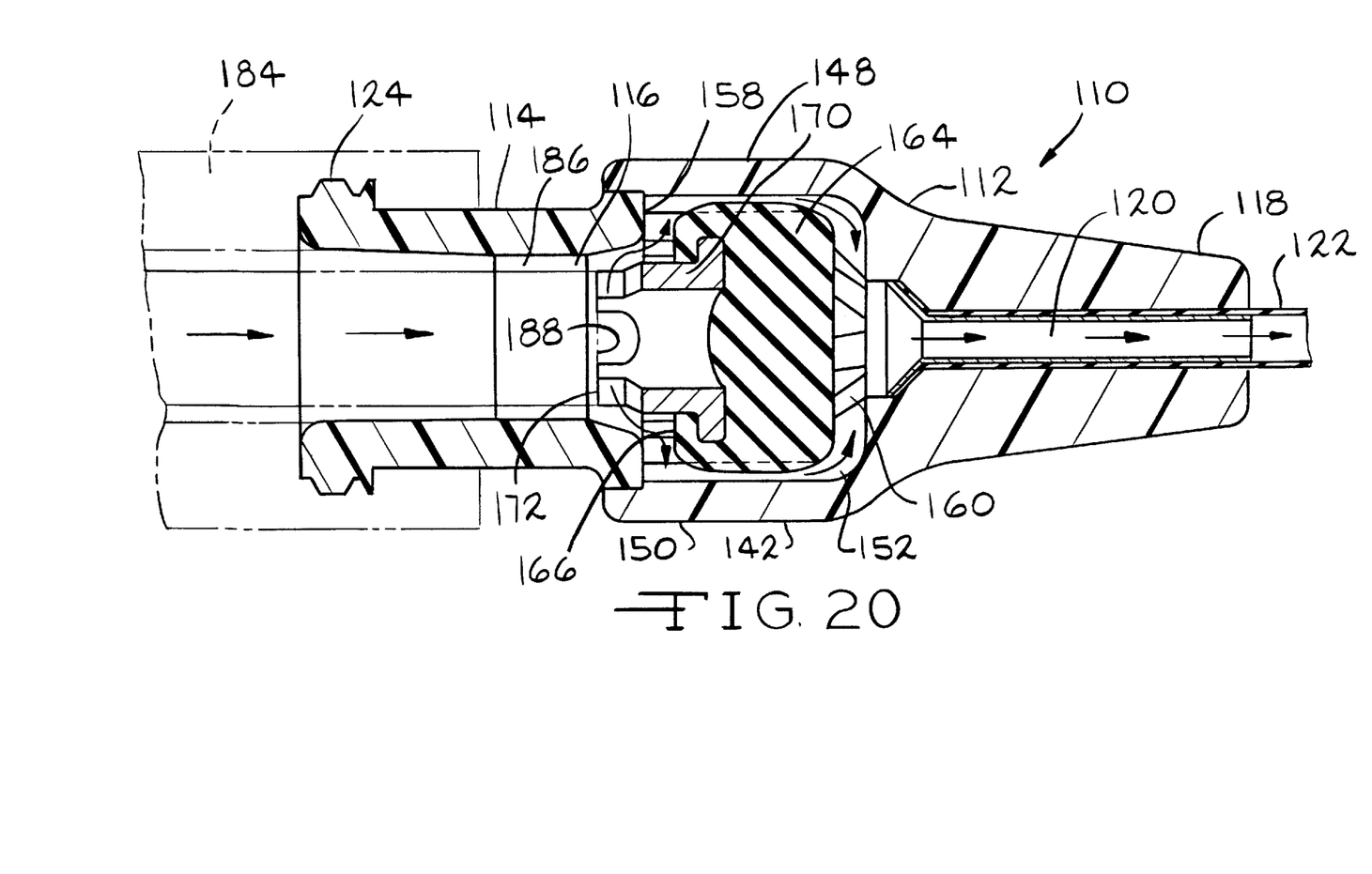
FIG. 20 is a view similar to the view of FIG. 19 showing the valve in an open position.

Referring to FIGS. 18, 19 and 20, a conventional luer 184, conforming with American National Standard Institute No. ANSI/HIMA MD70.1-1983 relating to luer lock fittings, can be attached to the connection end 114 of the housing 112. The luer 184 is in communication with, for example, intravenous tubing (not shown) that is connected to a supply of intravenous fluid (not shown).

Referring to FIGS. 19 and 20, the luer 184 includes a luer projection 186 that extends into the first fluid passageway 116 of the housing 112. The luer projection 186 includes an actuator surface 188 that engages the luer end 172 of the actuator 170. Movement of the luer 184 with respect to the connection end 114 of the housing 112 results in corresponding movement of the actuator 170. This movement causes the actuator 170 to move the valve 164 from the closed position as shown in FIG. 19 to the open position as shown in FIG. 20. As previously described, the valve 164 is comprised of a resilient material. Therefore, the valve can be compressed, as shown in FIG. 20, to allow the actuator end 166 of the valve 164 to become disengaged from the annular shoulder 158. Intravenous fluid is allowed to flow in the direction indicated by the arrows in FIG. 20 when the valve 164 is in the open position. This allows the intravenous fluid in communication with the luer 184 to pass through the catheter hub 110 into the blood vessel of the patient. It should also be understood that blood or some other bodily fluid can be drawn from the patient through the catheter hub 110 with the valve 164 controlling the flow of the fluid between the first and second fluid passageways 116 and 120, respectively. When the luer 184 is moved away from the actuator 170, the actuator end 166 of the valve 164 engages the annular shoulder 156 to reseal the valve chamber 152 as shown in FIG. 19.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. An apparatus, comprising:
    a needle protector including a body having a first end and a second end, said body including a plurality of side walls extending between said first and second ends in a first geometric configuration, said side walls defining an interior space, said side walls defining a first slot and a second slot;
    a needle hub having a front end, a back end, a first side and a second side being positioned in said interior space, said front end being adapted to receive a needle, said first and second sides each including handle means, said handle means extending through said slots to positions outside of said body;
    a needle in communication with said front end of said needle hub;
    a catheter hub including a housing having a connection end defining a first fluid passageway and a catheter end defining a second fluid passageway, said housing including at least one hub wall defining a valve chamber;
    valve means positioned in said valve chamber for controlling fluid flow in both directions through said chamber between said first and second fluid passageways; and
    actuator means for actuating said valve means.

2. The invention of claim 1, wherein said first end includes a plurality of threads.

3. The invention of claim 1, wherein one of said side walls includes a plurality of spaced projections.

4. The invention of claim 1, wherein said first geometric configuration is a polygon.

5. The invention of claim 4, wherein said polygon is a hexagon.

6. The invention of claim 1, wherein said slots are opposed in relation to one another.

7. The invention of claim 1, wherein each of said slots includes a locking portion adjacent said second end.

8. The invention of claim 1, wherein said needle hub includes a hub fluid passageway extending between said front and back ends.

9. The invention of claim 8, wherein said back end includes absorbent means.

10. The invention of claim 1, wherein said handle means consists of a wing and a handle member having an exterior surface and an interior surface.

11. The invention of claim 10, wherein each handle member includes a plurality of spaced grips on said exterior surface.

12. The invention of claim 10, wherein said handle member includes at least one locking projection on said interior surface.

13. The invention of claim 12, wherein said needle protector includes an end cap having a first leg and a second leg, each of said legs defining a locking recess for receiving said locking projections.

14. The invention of claim 8, wherein said needle defines a needle passageway in communication with said hub fluid passageway of said needle hub.

15. The invention of claim 1, wherein said catheter end of said catheter hub includes a catheter consisting of a polymeric material.

16. The invention of claim 2, wherein said connection end includes a plurality of threads for mating with said plurality of threads of said first end to attach said catheter hub to said needle protector.

17. The invention of claim 1, wherein said connection end defines an annular shoulder adjacent said valve chamber.

18. The invention of claim 1, wherein said housing includes a top and a bottom, one of said hub walls being planar at said bottom.

19. The invention of claim 1, wherein said housing includes a plurality of hub walls arranged in a second geometric configuration, said second geometric configuration is a polygon.

20. The invention of claim 19, wherein said polygon is a hexagon.

21. The invention of claim 1, wherein said housing includes a valve seat positioned in said valve chamber.

22. The invention of claim 21, wherein said valve seat includes a plurality of fluid openings to allow for fluid flow between said valve chamber and said second fluid passageway.

23. The invention of claim 1, wherein said valve means consists of a valve comprised of resilient material, said valve extending substantially between said first and second fluid passageways.

24. The invention of claim 17, wherein said valve means consists of a valve comprised of resilient material having a substantially cylindrical configuration, said valve having an actuator end and a housing end, said actuator end being engaged with said annular shoulder, whereby actuation of said actuator means causes said actuator end to become disengaged from said shoulder to allow for fluid flow through said first fluid passageway, said valve chamber and said second fluid passageway.

* * * * *